Figure 1:
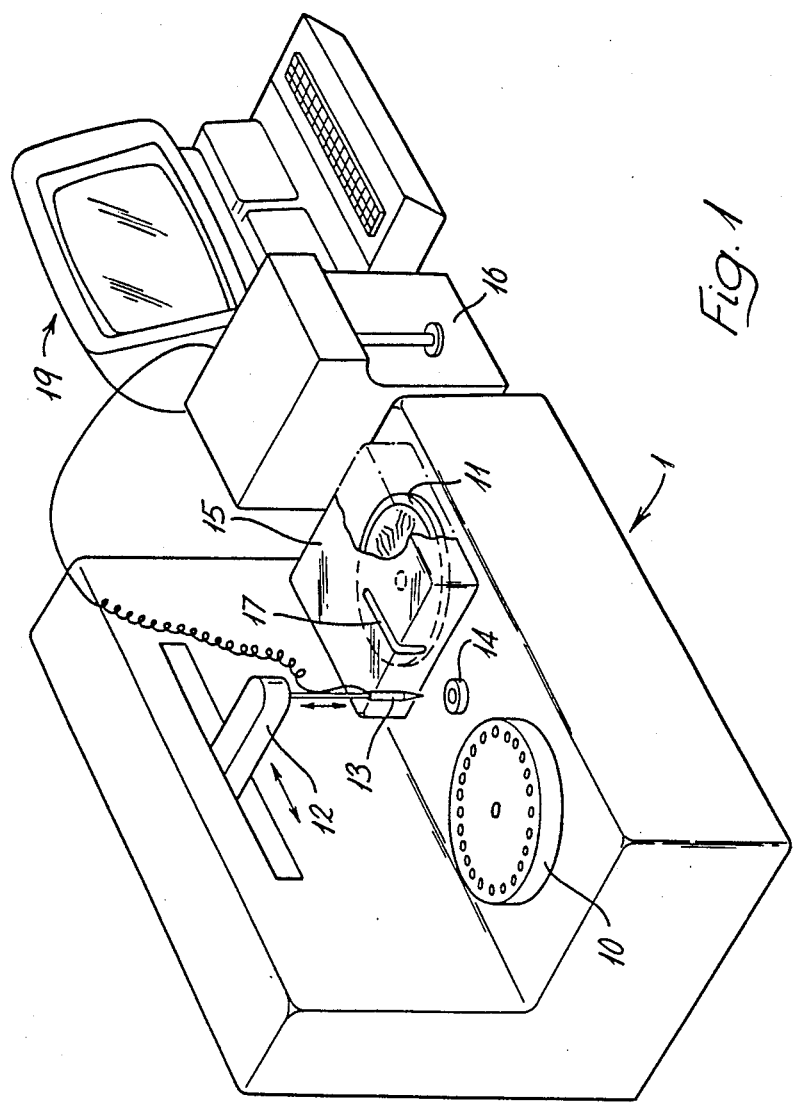

United States Patent [19]

Martin

[11] Patent Number: 4,961,915
[45] Date of Patent: Oct. 9, 1990

[54] AUTOMATIC CHEMISTRY MACHINE
[75] Inventor: William J. Martin, Sale, England
[73] Assignee: National Research Development Corporation, London, England
[21] Appl. No.: 815,054
[22] Filed: Dec. 31, 1985
[30] Foreign Application Priority Data Jan. 7, 1985 [GB] United Kingdom ............... 8500294

[51] Int. Cl.⁵ .................... C07H 15/12; C07H 17/00; B01J 14/00
[52] U.S. Cl. ...................... 422/116; 422/72; 422/129; 422/61; 436/45; 536/27
[58] Field of Search ............ 422/64, 67, 61, 72, 422/73, 102, 116, 129; 494/26, 27; 356/246, 426, 427; 436/45, 52; 536/27

[56] References Cited

U.S. PATENT DOCUMENTS

| | | | |
|---|---|---|---|
| 3,684,450 | 8/1972 | Adler et al. | 436/45 |
| 3,795,451 | 3/1974 | Mailen | 422/72 |
| 3,884,641 | 5/1975 | Kraffczyk et al. | 422/58 |
| 4,007,010 | 2/1977 | Woodbridge | 422/61 |
| 4,052,164 | 10/1977 | König | 422/72 |
| 4,065,263 | 12/1977 | Woodbridge | 422/57 |
| 4,095,948 | 6/1978 | Hunziker | 436/53 |
| 4,225,558 | 9/1980 | Peterson et al. | 422/72 |
| 4,279,862 | 7/1981 | Bretaudiere et al. | 494/27 |
| 4,308,028 | 12/1981 | Elkins | 422/102 |
| 4,314,968 | 2/1982 | Guigan | 436/45 |
| 4,325,910 | 4/1982 | Jordan | 422/65 |
| 4,344,768 | 8/1982 | Parker | 422/72 |
| 4,451,433 | 5/1984 | Yamashita et al. | 422/64 |
| 4,456,581 | 6/1984 | Edelmann et al. | 422/102 |
| 4,472,498 | 9/1984 | Masuda et al. | 422/56 |
| 4,515,889 | 5/1985 | Klose | 436/45 |

OTHER PUBLICATIONS

"Critical Reviews in Analytical Chemistry", Malmstadt et al., Chemical Rubber Company, 1972.

Primary Examiner—Michael S. Marcus
Attorney, Agent, or Firm—Cushman, Darby & Cushman

[57] ABSTRACT

An automatic chemistry machine particularly suitable for the automatic sequencing of DNA on the microliter scale including a source of reagents, a common means to transfer by contact microliter quantities of reagent, below 5 microliters, and a rotatable reaction surface to which said quantities of reagent are transferable, means to control the transfer means to access and contact specific spaced areas of the reaction surface, and means to control the rotation of the surface with regard to the transfer means action, the surface being formed to constrain flow of transferred reagent quantities over the surface and in a reaction area to mix under centrifugal action on faster rotation of the surface.

27 Claims, 5 Drawing Sheets

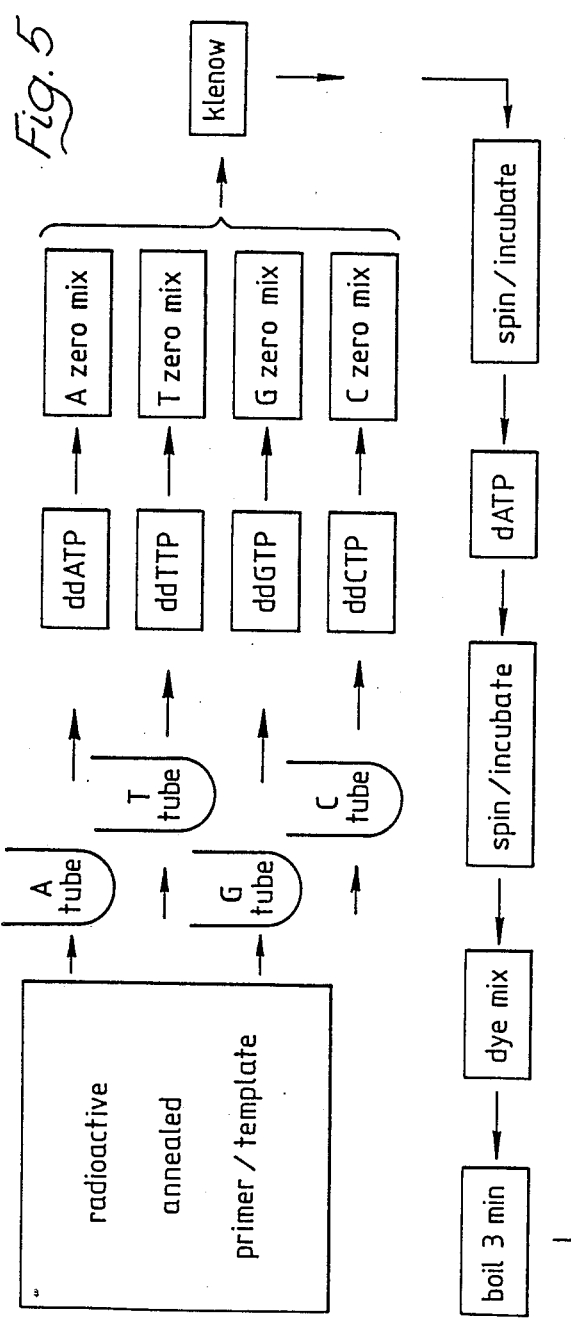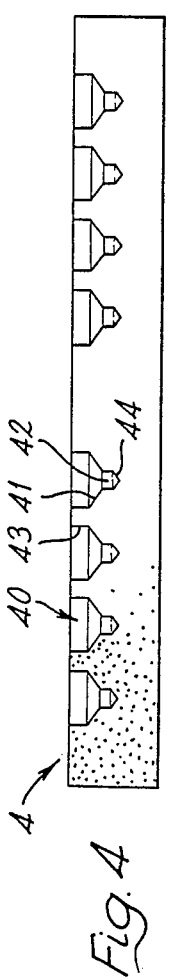

AUTOMATIC CHEMISTRY MACHINE

This invention relates to automatic chemistry machines.

Automatic chemistry machines have, in recent years, been the subject of considerable work in the field of analysis as the need to reduce the expenditure on skilled operators and the need to remove the variability and errors of such operators, however skilled, has led to attempts to carry out routine chemical procedures automatically. There is also a need to speed up procedures both to save operator time and make results available more quickly. Many mechanisms and techniques have been proposed including conveyors, turntables and shaking tables among others to convey vessels for reactions and suction, air bubbles and centrifugal action to move reagents through tubes. The clear conclusion from some twenty or more years of intensive work is that the automatic performance of any given chemical analysis procedure is not arrived at without a great deal of thought and experiment, usually requiring knowledge and experience of several scientific disciplines in one individual or group.

The technique for sequencing of DNA raises immense problems because of the sheer number of base-pairs involved and the need for absolute accuracy at every stage. The amount of information contained in a DNA molecule is enormous and it can take several years of work to determine the data contained in a molecule and enter it into a computer.

In DNA sequencing techniques microscopic quantities of reagent are handled in numerous tests to produce various DNA molecules. For economic reasons it is necessary to use microliter quantities and the chemical procedure requires that measured quantities of various reagents are mixed in a particular order and with intermediate timed reaction intervals.

It is an object of the invention to provide an automatic chemistry machine particularly suitable for the chemical techniques of DNA sequencing and also generally suitable for the measurement, deposition, mixing and reaction of microliter volumes of reagents.

According to the invention there is provided an automatic chemistry machine including:
  a rotatable reaction surface and means to support and rotate said surface,
  means to deposit reagents on said surface by contact,
  said surface including a smooth reaction area with alongside elongate radially extending flow constraining means to constrain said deposit reagents on rotation of the surface to flow freely over the reaction area in a radial direction and mix.

According to the invention there is also provided an automatic chemistry machine for the automatic sequencing of DNA on the microliter scale including a source of reagents, a common means to transfer, by contact, microliter quantities of reagent, below 5 microliter, and a rotatable reaction surface to which said quantities of reagent are transferable, means to control the transfer means to access and contact specific spaced areas of the reaction surface, and means to control the rotation of the surface with regard to the action of the transfer means, the surface being formed to constrain flow of transferred reagent quantities over the surface and in a reaction area to mix under centrifugal action on faster rotation of the surface.

The reagent quantities may be between 1 and 5 microliters for each reagent.

The surface may be a plate radially grooved or raised to receive reagent at spaced parts of the groove.

A microvolume reagent transfer device may be used to transfer reagent and/or deposit reagent in controlled volumes by contact with the surface.

According to one aspect of the invention there is provided an apparatus for carrying out chemical reactions under automatic control, the apparatus supporting side-by-side a rotary reagent store and a rotary reaction surface with a contact reagent transfer means operable along a path radial over the surface to transfer selected reagents from the store for deposit on the reaction surface at selected respective positions by contact with the surface, the reaction surface being supported for rotation at a first, loading speed and at least a second higher, mixing speed, the reaction surface being formed to constrain the flow of reagents over the surface and in a reaction area to mix on rotation of the surface at a higher speed, the apparatus further including means to drive the reagent store, transfer means and reaction surface and control means settable and operable to coordinate the drive of the store, transfer means and surface to produce desired selective transfer of reagents to respective surface positions, the control means being further settable and operable to rotate the surface at a higher speed to mix the reagents and thereafter selectively transfer further reagent to the surface for further mixing.

According to the invention there is further provided a method of carrying out chemical reactions with microliter quantities of reagents including providing a source of reagents, providing a reaction surface, individually transferring controlled microliter quantities of reagents for a reaction from the source and depositing said controlled quantities spaced apart on the surface, and causing or permitting the deposited reagents to move together over the surface to bring about a desired reaction.

The reaction surface may be shaped so that movement in a specific manner causes deposited reagents to move in a controlled manner.

For example a disc of inert material may have at least one generally radial groove so that, on rotation of the disc, reagents deposited along the groove move under forces generated by the rotation of the disc to mix and react.

Conveniently if a sequence of reactions involving the addition of reagents at intervals is required earlier reagents may be deposited away from the centre of the disc and later reagents deposited inwardly of those already deposited so that contamination of any contact transfer means is avoided and any reaction does not start until rapid rotation of the disc moves the latest reagent.

A disc or other reaction surface may be prepared with reagents in advance of use and stored away from the machine in a suitable cool place to preserve the reagents.

The apparatus may include means to control the temperature of the reagents held in the reagent source. This may include means to supply heating or cooling or may be means to contain a cooling mixture such as aqueous urea or a dry ice/organic solvent mixture. Electrical or electronic heating and cooling may be used, e.g. the Peltier effect. The temperature of the reaction area and surface may also be controlled, generally or locally.

The transfer device may be controlled to move to different specific points on a radial path over the reaction surface to order the deposit of reagents.

Figure 2:
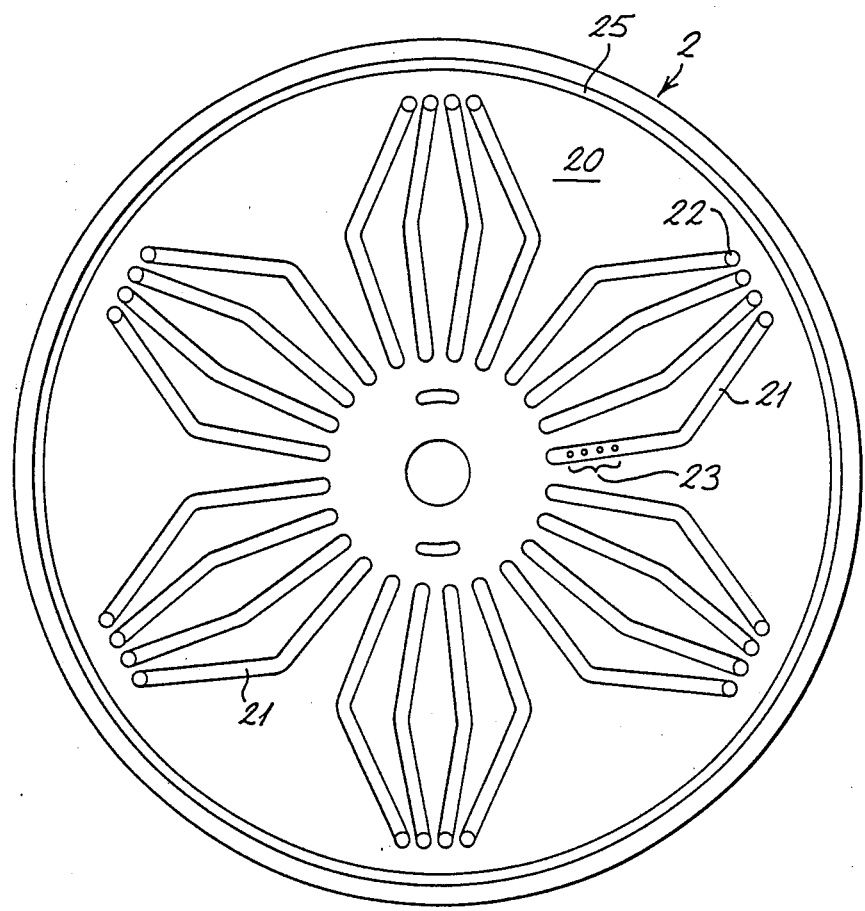
Figure 3:
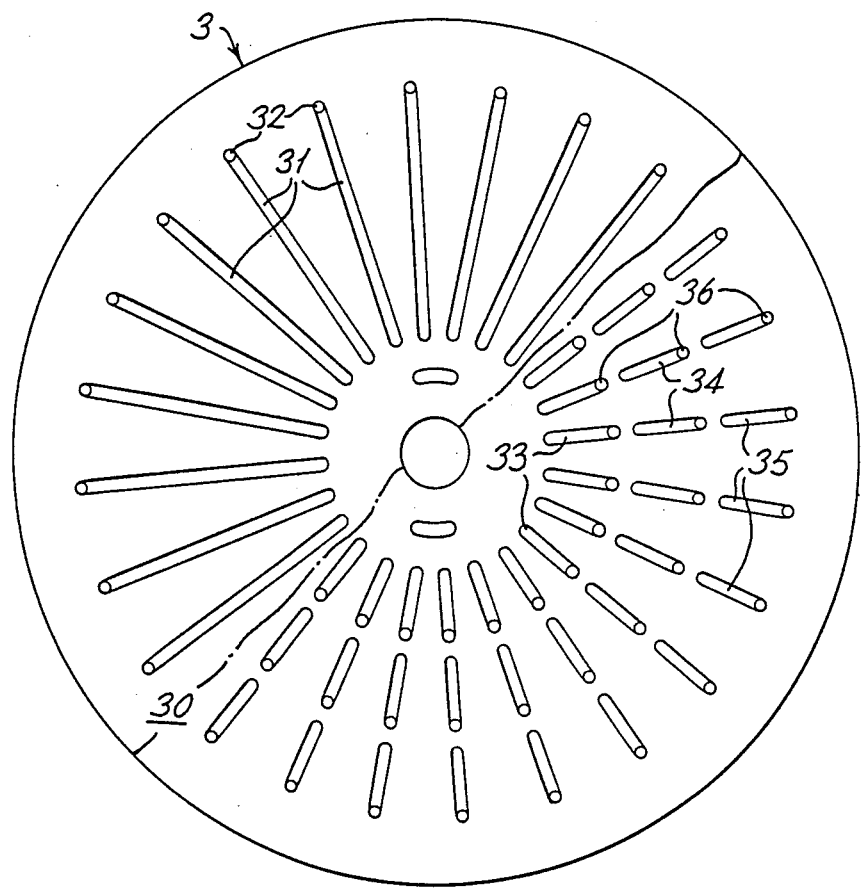
Figure 6:
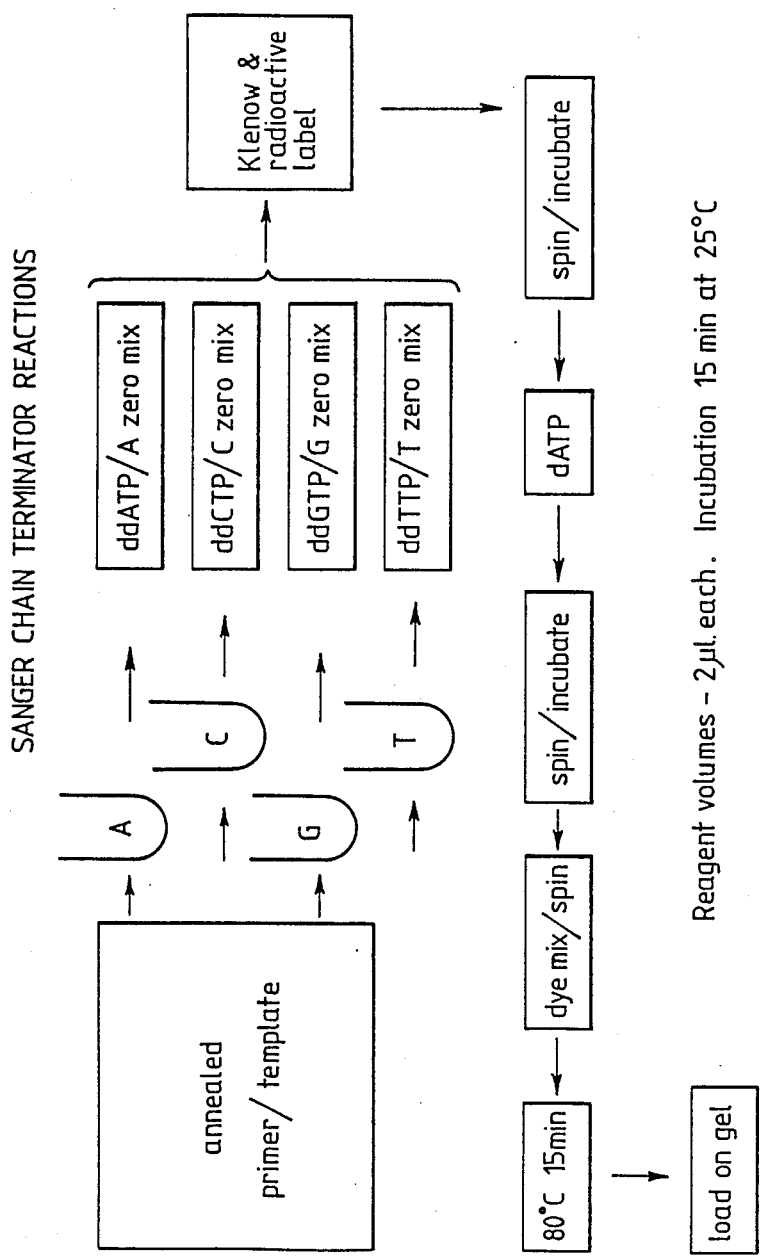

Embodiments of the invention will now be described in which:

FIG. 1 is a schematic view of an automatic chemistry arrangement embodying the invention, FIG. 2 is a plan view of a reaction surface, FIG. 3 shows in partial plan views two further reaction surfaces, FIG. 4 is a cross-section of another reaction surface, FIG. 5 is a flow chart of a reaction which can be automatically carried out with the invention, and FIG. 6 is a flow chart of another such reaction.

Various machines for automatic chemistry are well-known. One such is GEMSAEC, widely described in the literature, devised about 1969 at Oak Ridge Laboratory under the direction of Norman Anderson for fast chemical analysis work using photometric observation of results. The essential feature of GEMSAEC was a turntable thick enough to house vertical or inclined wells for reagents and samples. The wells held up to 300 microliter (0.3 milliliter) of reagent and as little as 1 microliter of sample, for reaction with the reagent, was stated to be needed. The wells were separated by weirs so that the reagents and samples could not flow and mix. The wells were arranged in a radial line with a chamber for optical examination at the outer end of the line. The chamber was linked by a tube formed by a bore through the turntable material to the nearest well. In operation the reagent of largest volume, in the innermost well of a line, could be forced over the weir to the next outer well by rotating the turntable rapidly enough. The reagent mixed with the sample and the mixture was displaced through the bore to the chamber. The bore ensured adequate mixing. Once in the chamber, the chemical reaction proceeded under observation as appropriate.

FIG. 2 shows a reaction surface 2 embodying the present invention. A thin circular slab 20 of material such as PTFE is made suitable for rotation about its centre and the surface is formed into simple grooves such as 21 to provide reaction areas. A peripheral groove 25 is also provided. The slab is about 20 cm diameter and 1 cm thick. The grooves are smooth and regular in cross-section. As shown 24 grooves are in six groups of four. The grooves have a width of about 5 millimeters. More grooves can be used, e.g. 50 as 12 groups of four and two diametrically opposite blank grooves. The grooves, in the illustrated example, extend radially initially and then converge onto respective closely-spaced recesses 22 at the outer end of each groove, the recesses being in a straight line. This arrangement is not essential but is convenient as ganged four-probe liquid micro-probes are available readily and these can be used to extract the reacted chemicals. Other arrangements can be used but the inner part of the groove is preferably radial. The groove shape must prevent reagent or sample escape sideways when the speed of rotation changes. An important reason for the radial shape is that it eases the accurate deposition of reagent. The four dots indicated at 23 represent four discrete positions where reagents or samples can be deposited and remain where deposited for subsequent movement on rotation of the surface 2, about its centre, to then mingle and interact and end up in the respective recess 22. Clearly more positions can be used if needed. Positions nearer the centre can be used, when earlier deposited reagents or samples have been mixed by rotation, to avoid contamination. Any suitable microliter delivery system can be used but it is particularly convenient to use one in which an arm can be controlled to move along a radius of slab 20 by distinct increments to deposit microliter quantities of respective reagents or samples at each of positions 23. This produces a common delivery system.

In use, reagents are deposited by contact between the probe and the disc surface at spaced positions, to avoid cross-contamination, and the slab 20 is then rotated at about 1700 r.p.m. for about half a minute to move the reagents to the recesses and mix them. The reagents are then left for about 15 minutes at ambient temperature (some 18° C.) to allow the reaction to run to completion. If required, after a mixing rotation of the slab, further reagents can be deposited at intervals during a reaction period and moved to the recesses by a further short, fast, rotation of the slab. The material accumulated in recesses 22, about 10 microliters in each case, is then removed with a suitable probe for further treatment, e.g. electrophoresis in a gel. Care must be taken to minimise evaporation of reagents by ensuring that they are not exposed for unduly long periods on the reaction surface. A closefitting cover (not shown) may be fitted over the recesses to shield the reagents therein and to reduce evaporation. When radioactive reagents are used the cover is necessary to prevent spray escaping.

FIG. 1 shows a complete apparatus embodying the invention for the automatic handling of reagents in DNA sequencing. Many of the mechanical and electrical details will be well-known and readily apparent to those skilled in the art and will not be described.

A case 1 houses two circular platforms 10, 11 which are supported for controlled motion about their respective axes. Platform 11 is essentially the item shown in FIG. 2 and will be described later. Platform %0 is a reagent disc housing supplies of reagents in distinct tubes or cavities, which platform can be controllably moved by rotation to specific positions. Between the two platforms is a support 12 for a microliter probe 13. Support 12 is arranged to move probe 13 on the line of centres of platforms 10 and 11. Platform 11 has a cover 15 with a slot 17 for probe 13.

Platform 10 can be of any suitable form but is preferably arranged to provide a controlled temperature environment for the reagent supplies. Conveniently the latent heat of liquidification of a frozen material can be used to provide some degree of temperature control. The bags of material commercially available to cool picnic boxes are suitable and can maintain the platform 10 at or below 0° C. for several hours, without the need for cooling devices in the apparatus. Other cooling mixtures can also be used for specific sub-zero temperature ranges. The Peltier effect can also be used for heating or cooling. Heating and cooling can be selective on both platform 10 and platform 11.

Dilution or preliminary mixing of reagents can be carried out on platform 10 in preparation for deposition, the mixing and reaction implemented in platform 11. On platform 10 conventional non-contact deposition can be used, e.g. with the microliter probe, to prevent cross-contamination of the probe.

Platforms 10 and 11 are operated by stepper motors to be indexable to bring any reagent tube or cavity of platform 10 and any radial groove of platform 11 on the line of action of probe 13 on support 12. In this way a chosen reagent from platform 10 can be placed at an appropriate point on platform 11 along a groove.

The manner in which platforms 10 and 11 and support 12 are moved and controlled will be readily apparent and not described further.

Platform 11 can also be rotated much more rapidly, as described with reference to FIG. 2, to mix the reagents and bring about the desired chemical reaction.

The microliter probe 13 is attached by a tube to a proprietary device shown at 16, such as the Microlab M (Hamilton) (RTM) having an accurate syringe to deliver volumes as small as 0.1 microliter. A probe cleaning weir is shown at 14. The cleaning weir has one part supplied with clean water to flow over the weir into a waste area and drain. The probe when dipped in the one part displaces water, to wash the probe and prevent cross-contamination. In operation the probe is supplied with a cleaning liquid. Some liquid is first expelled to clean the inside of the probe and the probe then dipped in the cleaning weir 14 to clean the outside and then withdrawn. An air bubble is then drawn into the probe tip to provide isolation from the cleaning liquid. The probe tip is then caused to move over and dip into a reagent in platform 10 and some reagent is collected by drawing back the liquid and air bubble in the probe. Some 10 microliters is conveniently collected. The probe is then moved over platform 11 which is rotated as appropriate and the probe moved radially to the required position along a groove. Some 2 microliters of reagent is then discharged from the probe by pushing the liquid and air bubble forward. This small quantity of reagent cannot form a drop and is transferred to platform 11 by touching the probe on the surface. Further small quantities of reagent can be transferred elsewhere on the platform. Other reagent quantities are possible, typically in the range 1 to 5 microliters, but less or more may be needed in some applications. By a suitable sequence of movements, conveniently under the control of a microprocessor or the like, the platform 11 is supplied with the required disposition of reagents. Stepping of platform 11 is then changed to high speed rotation to bring about the mixing of the reagents and the reaction. The recesses may taper and be curved to contain the mixed reagents and collect them for easy removal.

The exact speed profile can be adjusted to suit particular circumstances but in general a steady "ramp" of speed build up is desirable between the stepping speed and the mixing speeds. Too steep a ramp could lead to loss of reagent as spray or even displace the reagents sideways. If suitable controls are available an initially steep build up of speed followed by a slower approach to top speed is useful. Closed loop control would be advantageous.

Heating, or cooling, can be applied to the reagents in position on the reaction surface or when mixed to provide a specific temperature for a chemical reaction. It can be useful to keep the surface spinning slowly during a reaction to assist mixing and to produce even heating.

Subsequently platform 11 can be removed for further processing of the reacted reagents and then cleaned for re-use. Alternatively a disposable platform can be used, e.g. a plastic moulding. Suitable locking and release arrangements will be apparent.

Deposition of reagent by always touching the probe on a clean part of the reaction surface ensures that the probe is not cross-contaminated and this reduces wash requirements.

The apparatus conveniently uses five stepper motors. One steps round and spins platform 11, another steps round platform 10. One moves support 12 and another drives the probe downwards and upwards from support 12. A fifth motor (in the Microlab M) measures and dispenses liquids from the probe. A suitable motor drive control system can readily be devised and appropriate instructions prepared and stored in a microcomputer 19 such as an Apple IIe or IBMPC (RTMs). The correct location of a reaction surface can be produced by keying it to the drive shaft and providing an indexing rotor fast on the drive shaft with a single radial slot in the rotor to identify an index position. When the motor stops after a high speed action it is then driven slowly until the index slot is detected by a sensor to cause the motor to stop with the reaction surface at a repeatable reaction surface position for the probe.

FIG. 3 shows two other alternative versions of the rotatable reaction surface. In one version the reaction surface 30 of the slab 3 is formed to constrain the flow of reagent in reaction areas of straight radial grooves each of which, such as 31, has a small recess 32 at the outer end. The slab is a similar size to the one described above. No peripheral groove, such as 25 in FIG. 2, is provided as this was to prevent water from a heating bath under the slab being spilled onto the reaction surface and contaminating the reagents. The straight grooves have a rectangular cross-section and are about 3 millimeters wide and 2 to 3 millimeters deep. The sides are steep or vertical to prevent reagents in the groove escaping when the slab is rotated to mix the reagents.

It is possible to provide several separate grooves along a single radial direction, as outlined for the other version in FIG. 3 where grooves 33, 34, 35 are in a single radial direction, separate with respective end recesses 36 from each other. In use it is possible to rotate the slab at specific speeds in a group so that at the slower speed first the outermost set of spacedly deposited reagents is mixed then at a higher speed the next inward set of reagents and so on. Speeds such as 500, 900 and 1600 r.p.m form one possible group. Clearly the exact values will depend on the dimensions of the slab and groove position. It will be apparent that such a multiple groove system permits quite complicated operating regimes to be set up with one set of reactions being started a set time after another, for example, the reagents having been deposited in a single process. Reactions which require different incubation times can thus all be caused to be completed at one time. The exact regime is of course for the operator of the chemical process to decide from the facilities made available by the versatility of the apparatus. It may be convenient to load a further set of reagents while a previous mixture is reacting or incubating, as the stepping action can be useful to agitate the reacting mixture. The heating action should be confined to the recesses so three ring-like heaters can be used for this embodiment. The heating should not be applied so that reagent can evaporate before mixing.

The terminal recesses 22 are shown as being in groups of four in a straight line but, as mentioned above, this is only for one particular ganged probe and in FIG. 3 the recesses, 32, 36, are positioned on a circle centred on the slab centre. The recess walls can be vertical or inclined.

Other forms of surface are possible which will constrain reagents to a reaction area on rotation of the surface. Radial raised portions such as ribs, walls, or ridges on the surface which leads to recesses will constrain the flow of reagents when the surface accelerates so that the reagents flow into a recess at an outer end under centrifugal action and mix. If the direction of rotation is fixed only one wall, rib or ridge is required for each group of reagent deposits that are to mix.

The material of the reaction surface needs to be chosen with care. It is essential that there is no reaction between the surface material and the reagents, some of which are chemically very active. Polytetraflorethylene is a suitable material although not particular easy to work or cheap to buy. Dimensional stability could be a problem. Polypropylene is another material which is useful as it can be worked accurately and does not creep. A silicone coating may be used to resist chemical action and in this way less inert materials may be used for the body of the reaction surface. Disposable surfaces may also be used, again with a coating if needed. If the reaction surface is to be heated or cooled then suitable techniques may be applied for the construction of the surface.

Another form of washing arrangement for the transfer probe is possible. By placing the probe in a conforming cup and squirting cleaning liquid from the probe into the cup the outer side of the probe is washed by liquid swirling in the cup. When radioactive reagents are involved three washes are needed and all waste liquids must be disposed of properly.

In another version platform 11 is changed to four or more plates, one shown at 4 in FIG. 4, pivoted on a frame (not shown) to swing when the frame is rotated about the axis of the frame somewhat in the manner of a centrifuge. Each plate, which is conveniently square or rectangular, has an array of reaction areas (40) each having conical surfaces 41 leading to a recess 42. FIG. 4 shows a cross-section through one row in the array. The conical surface 41 is capable of receiving spaced microliter quantities of reagent, say four around the cone, and a fifth reagent may be placed in the recess. On rotation of the frame the pivoted plates swing to an angle at which the four reagents move into the recess to react with each other and any fifth reagent if present.

Typically each reaction area is a cavity 43 some 9 mm in diameter leading to the conical surface 41 which reduces the cavity to the recess 42 which is some 3 mm in diameter and about 3 mm deep, 1 mm of which depth is formed by a closed conical surface 44. The overall depth is some 8 mm. The areas are closely spaced (some 12 mm centres) in a block of about 15 mm thickness and 128 mm by 85 mm.

In both versions the microliter quantities cannot move over the surface until subject to large forces on rapid rotation so no definite containers are needed nor any special mixing bores.

FIG. 5 is a chart of a particular chemistry that the above apparatus is particularly suitable for.

The general form of the Sanger Chain Terminator reaction shown in FIG. 5 is well-known. However a variant is shown in FIG. 6 which is particularly appropriate for a machine such as is described above. Reaction surface discs can be prepared with primers automatically deposited in specific areas and then stored at −20° C. for 3 months. The template can then be added and the primer/template annealed. In this form the disc will keep for 2 days at zero degrees centrigrade. For use the disc with annealed primer/template has an appropriate combined dideoxy/zero mix automatically deposited and a radioactive label added with the "Klenow" fragment. These and further steps are all automatic, up to the addition of the dye and the mix and spin action. The 15 minute period at 80° C. is manually controlled as is the loading onto gel for electrophoresis. However either or both of these steps can be automated.

To carry out the FIG. 6 reaction on the reaction surface with multiple rings of areas superimposed deposition of some reagents can be used. Separate spaced deposition is used as far as the Klenow and radioactive label step. The primer/template and the zero mixes are deposited in outer positions with the Klenow in the innermost positions. These initial reagents are spun mixed and incubated then the dATP is deposited where the Klenow was initially deposited and is spun mixed and incubated in turn to so that the dye can be deposited in its place for the next mixing step. Cross-contamination does not occur if the deposition probe touches a reagent deposition area where that reagent, such as dATP or Klenow, has been added to all the mixing cavities. Clearly such an area must be an inward one so that other reagents flow through them. Superimposed deposition permits the use of shorter reaction areas.

In particular the use of such small quantities reduces the ability of the deposited reagent to flow and in general ensures that no flow or mixing can occur until the surface is spun. No special shaping of the surface to keep deposited reagents in place is needed, apart from that to prevent lateral movement on acceleration so the surface can be simpler and cheaper to make and, if reusable, easier to clean.

The techniques provided by the invention are also useful for other chemistries that require the mixing of small quantities of reagents, with or without intervening mixing periods, such as those employed in DNA restriction mapping.

It will be appreciated that the exact sequence of operations such as reagent deposit position and sequence, spin speeds and duration, directly heating and cooling actions can be selected to permit a specific chemical procedure to be carried out automatically. Among these are "T-tracking", primer template annealing and "cloning" reactions. When the automatic chemistry machine is connected to a microcomputer or the device various specific chemical procedures can be stored in the microcomputer and called up from a "menu" to control the machine as required. Reagent selection can also be controlled in this way.

Reaction surfaces can be prepared in advance with some or all reagents and stored in a suitably cool place such as a freezer or refrigerator until required. The reagents would be the microliter quantities deposited at spaced positions on the reaction surface. In this way less common reagents can be kept available without the need for preparing and storing the reagents, which are often of short life, locally for each use. By using controlled heating of the reaction surface chemical reactions can be triggered. For example a reaction starting at 37° C. can be triggered by raising the reaction surface to 40° C. and then stopping the supply of heat or sensing the temperature and controlling the supply of heat.

Reagent storage discs, i.e. platform 1, can be similarly prepared in advance and stored safely. Only the templates have to be added to use the disc. As the templates are specific to a particular reaction a specific group of storage compartments can be provided which are filled and fitted in the disc in the users laboratory. When used these can be removed and different templates fitted in their place so that the "common" reagents already in the disc can be drawn on to the best possible extent.

I claim:

1. An automatic chemistry machine comprising:
a rotatable reaction surface,
means for supporting and rotating said reaction surface at a first loading speed and at least at a second faster mixing speed, said reaction surface consisting essentially of one or more reagent paths having a predetermined length,
reagent supply means for supplying reagents,
means for depositing predetermined microliter amounts of selected reagents at predetermined spaced apart points along the length of said reagent path,
each of said reagent paths consisting essentially of including a substantially horizontally longitudinally extending reaction area having a bottom surface situated on a common plane and terminating at a radially positioned outer end including means defining a cavity and being further comprised of reagent constraining means for constraining the deposited reagents so that upon rotation of said reaction surface at said mixing speed the deposited reagents will be constrained chordally yet flow freely over the reaction path in a radial direction and mix together.

2. A machine according to claim 1 in which the means in the surface to constrain the reagents is at least one raised part.

3. A machine according to claim 2 in which the raised part of the surface is one of a ridge, rib and wall.

4. A machine according to claim 1 in which the means to deposit reagents deposits only controlled microliter quantities by contact of a liquid-carrying probe with said surface.

5. An apparatus according to claim 1 in which said means to rotate the reaction surface is effective to rotate that surface in a stepwise manner.

6. A machine as in claim 1 wherein said reaction surface includes a plurality of reagent paths each having a plurality of discrete, spaced apart reagent deposit regions, said reagent depositing means includes a liquid-carrying probe and means for controlling the movement of said liquid-carrying probe relative to said reaction surface and said reagent supply means to acquire a predetermined quantity of a selected reagent and to deposit five microliters or less of reagent on a preselected one of said plurality of deposit regions.

7. A machine as in claim 1 wherein said reaction surface includes a plurality of radially extending channel means each having a smooth surface over which deposited reagents can freely flow.

8. A machine is in claim 1 wherein said reagent supply means includes a plurality of reagents.

9. A machine according to claim 1 in which each path is a radially extending groove having sides walls form said constraining means which constrain the reagents chordially.

10. A machine according to claim 9 in which the groove is straight.

11. A machine according to claim 9 in which there are groups of grooves.

12. A machine as in claim 1 wherein said at least one path extends substantially radially.

13. A machine as in claim 12 wherein said at least one path has inner, central and outer portions.

14. A machine as in claim 13 wherein said outer portion terminates at means defining a recess for receiving the mixed reagents.

15. A machine as in claim 13 wherein at least said inner portion includes a plurality of discrete, spaced apart reagent deposit region.

16. A machine as in claim 13 wherein said reaction surface includes a plurality of said paths arrayed in a plurality of groups uniformly spaced about said reaction surface with each of the said paths within each of said plurality of groups being spaced apart.

17. A machine as in claim 16 wherein the outer portions of said paths in each group are spaced from one another but converge inwardly toward a central point.

18. An apparatus to carry out DNA sequencing using microliter quantities of reagent chemistries under automatic control, said apparatus including side-by-side a rotary reagent store and means defining a rotary reaction surface consisting essentially of at least one smooth, radially extending reaction path having a predetermined length and a uniform cross-section along which deposited reagents can freely flow and terminating at a radially positioned outer end with means defining a reaction cavity, contact reagent transfer means operable along a radial path for collecting and transferring selected reagents from said store and for depositing such selected reagents on said reaction surface means at selected respective spaced apart positions along the length of said reaction path by contact with said reaction surface means, said reaction surface means being supported for rotation at a first, loading speed and at least at a second higher, mixing speed, said radially extending reaction path having a substantially horizontally extending reaction area in the form of a bottom surface situated on a common plane terminating at said reaction cavity and being formed to constrain the flow of reagents circumferentially beyond the reaction path so that the reagents mix as they flow radially along the reaction path following rotation of the said reaction surface means at said mixing speed to form a reacted product, the apparatus further including drive means for driving each of said reagent store, transfer means and said reaction surface means respectively, and control means for coordinating said drive means to properly position preselected reagents in a preselected sequence on said reaction path and to mix such reagents in the desired sequence.

19. Apparatus according to claim 18 in which said store includes a plurality of storage compartments and said reaction surface means includes a plurality of reaction paths.

20. An apparatus as in claim 10 wherein the means for collecting and depositing reagents is effective to deposit five microliters or less of each of the selected reagents.

21. An apparatus to carry out DNA sequencing using microliter quantities of reagent chemistries under automatic control, said apparatus including side-by-side a rotary reagent store including a plurality of storage compartments and means defining a rotary reaction surface consisting essentially of a plurality of smooth, radially extending reaction paths having pre-determined lengths and uniform cross-sections along which deposited reagents can freely flow and terminating at radially positioned outer ends with means defining a reaction cavity, contact reagent transfer means operable along a radial path for collecting and transferring selected reagents from said store and for depositing such selected reagents on said reaction surface means at selected respective spaced apart positions along the length of said reaction path by contact with said reaction surface means, said reaction surface means being supported for rotation at a first, loading speed and at least at a second higher, mixing speed, said radially extending reaction path having a substantially horizontally extending reaction area in the form of a bottom surface situated on a common plane terminating at said reaction cavity and being formed to constrain the flow of reagents circumferentially beyond the reaction path so that the reagents mix as they flow radially along the reaction path following rotation of the reaction surface means at said mixing speed to form a reacted product, the apparatus further including drive means for driving each of said reagent store, transfer means and said reaction surface means respectively, and control means for coordinating said drive means to properly position preselected reagents in a preselected sequence on said reaction path to mix such reagents in the desired sequence the apparatus further including means to selectively adjust the temperature of at least one of the storage compartments and to controllably heat said reaction paths, said temperature adjusting means including temperature control means operable to independently control the selected adjustment of the temperature of the storage compartments and of said reaction paths.

22. A method of automatically carrying out a sequence of chemical reactions under specific conditions with specific reagents including the steps of depositing volumes of five microliters or less of each of a plurality of selected reagents on a reaction surface for said reactions, rotating said reaction surface to mix the deposited reagents, controlling the temperature of the reagents and the reaction surface and maintaining the desired reaction surface conditions for a predetermined reaction time.

23. A reaction surface for an automatic chemistry machine comprising a substantially circular disk having a plurality of circumferentially spaced apart radially extending substantially planar areas, each of said areas being prepared with deposited volumes of five microliters or less of Sanger chain terminator reagents including ddATP, ddTTP, ddGTP and ddCTD reagents in selected spaced apart positions and cooled to a temperature to preserve said reagents for eventual use in a specific chemical reaction.

24. An automatic chemistry machine for the automatic sequencing of DNA on the microliter scale including a source of reagents, a common means to transfer, by contact, microliter quantities of reagent, and a rotatable reaction surface consisting essentially of a disk having a plurality of horizontally extending reaction areas to which said quantities of reagent are transferable, each of the reaction areas being defined by a substantially planar bottom surface and terminating at a radially positioned outer end, means to control the transfer means to access and contact specific spaced areas of said reaction areas, and means to control the rotation of said surface with regard to the transfer means action, said surface being formed to circumferentially constrain flow of transferred reagent quantities and allow radial flow thereof over the reaction area on said surface so that the transferred quantities mix under centrifugal action on faster rotation of said surface.

25. A method of carrying out chemical reactions with microliter quantities of reagents including the steps of providing a source of reagents, providing a reaction surface that can be rotated under controlled conditions, individually transferring controlled five or less microliter quantities of reagents from the reagent source and depositing said controlled quantities at spaced apart locations radially along the length of the reaction surface, moving the deposited reagents along the reaction surface to mix them together in order to bring about a desired reaction and collecting and withdrawing the reactive chemistries from the reaction surface.

26. An apparatus to carry out chemical reactions under automatic control, said apparatus including reagent store means for storing a variety of reagents and means defining a reaction surface having at least one smooth radially extending substantially planar path along which reagents can freely flow, contact reagent transfer means operable along a radial path for collecting and transferring selected reagents from said reagent store and for depositing one to five microliters of the selected reagents on said path at selected respectively spaced apart positions, respectively, by contact with said reaction surface means, said reaction surface means being supported for rotation at a first, loading speed and at least at a second higher, mixing speed, said reaction surface means consisting essentially of a substantially planar path and means extending parallel to the flow direction of the microliter quantities of reagents along that path to constrain the flow of reagents circumferentially beyond said radially extending path so that upon rotation at said mixing speed the reagents can flow along said radially extending path and mix, the apparatus further including drive means for driving each of said reagent store means, said transfer means and said reaction surface means, respectively, and control means for coordinating the drive means for said reagent store means, said transfer means and said reaction surface means to produce the desired selective transfer of reagents to desired surface positions along said path, said control means being operable to selectively transfer and mix reagent chemistries in an automatic, preselected sequence.

27. A method of automatically carrying out a sequence of chemical reactions under specific conditions with specific reagents including the steps of depositing one to five microliters of selected reagents so that the deposited reagents are spaced apart on predetermined portions of a smooth reaction surface, rotating the reaction surface at a speed sufficient to cause the deposited microliter volumes of reagents to flow freely along the smooth reaction surface and thereby mix together, adjusting the temperature of the reagents and the reaction surface, holding the reaction surface conditions for a predetermined reaction time, depositing further reagents on preselected portions of the reaction surface and rotating the reaction surface to mix the reagents and holding the reaction conditions for the reagents on the reaction surface.

* * * * *